United States Patent
Zuhars et al.

(10) Patent No.: US 10,905,496 B2
(45) Date of Patent: Feb. 2, 2021

(54) METHOD FOR CONFIRMING REGISTRATION OF TRACKED BONES

(71) Applicant: THINK SURGICAL, INC., Fremont, CA (US)

(72) Inventors: Joel Zuhars, Fremont, CA (US); Daniel P. Bonny, Fremont, CA (US); Saleh Tabandeh, Fremont, CA (US)

(73) Assignee: THINK SURGICAL, INC., Fremont, CA (US)

( * ) Notice: Subject to any disclaimer, the term of this patent is extended or adjusted under 35 U.S.C. 154(b) by 378 days.

(21) Appl. No.: 15/769,040

(22) PCT Filed: Nov. 15, 2016

(86) PCT No.: PCT/US2016/062008
§ 371 (c)(1),
(2) Date: Apr. 17, 2018

(87) PCT Pub. No.: WO2017/087371
PCT Pub. Date: May 26, 2017

(65) Prior Publication Data
US 2020/0237441 A1 Jul. 30, 2020

Related U.S. Application Data

(60) Provisional application No. 62/255,618, filed on Nov. 16, 2015.

(51) Int. Cl.
*A61B 34/20* (2016.01)
(52) U.S. Cl.
CPC ...... *A61B 34/20* (2016.02); *A61B 2034/2055* (2016.02)
(58) Field of Classification Search
CPC ........ A61F 2/46; A61F 2/4603; A61F 2/4607; A61F 2/4609; A61B 34/20;
(Continued)

(56) References Cited

U.S. PATENT DOCUMENTS

| 5,086,401 A | 2/1992 | Glassman et al. |
| 5,282,770 A | 2/1994 | Shibata |

(Continued)

FOREIGN PATENT DOCUMENTS

| CN | 102727309 A | 10/2012 |
| CN | 102933163 A | 2/2013 |

(Continued)

OTHER PUBLICATIONS

Besl, Paul J. and McKay, Neil D., "A Method for Registration of 3-D Shapes", IEEE Transactions on Pattern Analysis and Machine Intelligence, Feb. 1992, pp. 239-256, vol. 14, Issue 2, © 1992 IEEE; DOI: 10.1109/34.121791.

(Continued)

*Primary Examiner* — Eric S Gibson
(74) *Attorney, Agent, or Firm* — Blue Filament Law PLLC

(57) ABSTRACT

A process for confirming registration of bones involved in a joint replacement procedure is provided that includes a three dimensional (3-D) models of the bones being generated. The bones are tracked with a tracking device attached to each of the bones to allow 6-degrees of freedom (DOF) tracking during the joint replacement procedure. The 3-D models to the bones are registered and the bones having the tracking device are moved. A corresponding motion in the 3-D models with the moving of the bones is then observed. The registration of the 3-D models to the bone when the observations of the 3-D models move in correspondence with the actual bones is then confirmed or an alarm when an algorithm detects the 3-D bone models move unexpectedly during the movement of the bones. A system for confirming registration of bones involved in the joint replacement procedure is also provided.

13 Claims, 7 Drawing Sheets

(58) Field of Classification Search
CPC .... A61B 2034/2046; A61B 2034/2055; A61B 2034/2057
See application file for complete search history.

(56) References Cited

U.S. PATENT DOCUMENTS

| | | | |
|---|---|---|---|
| 6,033,415 A | | 3/2000 | Mittelstadt et al. |
| 6,061,644 A | * | 5/2000 | Leis .................. G01S 5/163 382/103 |
| 6,205,411 B1 | * | 3/2001 | DiGioia, III ............. A61F 2/46 703/11 |
| 6,322,567 B1 | | 11/2001 | Mittelstadt et al. |
| 6,529,765 B1 | * | 3/2003 | Franck .................. A61B 90/10 600/427 |
| 7,206,626 B2 | * | 4/2007 | Quaid, III ............. B25J 9/0081 600/407 |
| 7,302,288 B1 | | 11/2007 | Schellenberg |
| 8,774,900 B2 | * | 7/2014 | Buly ...................... A61B 5/103 600/427 |
| 8,876,830 B2 | | 11/2014 | Hodorek et al. |
| 8,961,536 B2 | | 2/2015 | Nikou et al. |
| 2004/0111183 A1 | * | 6/2004 | Sutherland ............. A61B 34/77 700/245 |
| 2007/0073136 A1 | * | 3/2007 | Metzger ............. A61B 17/1675 600/407 |
| 2010/0256504 A1 | * | 10/2010 | Moreau-Gaudry ...... A61B 8/08 600/476 |
| 2011/0069867 A1 | * | 3/2011 | Buehner ................ A61B 34/20 382/103 |
| 2011/0257652 A1 | | 10/2011 | Hughes et al. |
| 2013/0060146 A1 | * | 3/2013 | Yang ...................... A61B 6/032 600/476 |
| 2013/0060278 A1 | | 3/2013 | Bozung et al. |
| 2013/0211232 A1 | | 8/2013 | Murphy et al. |
| 2014/0171962 A1 | | 6/2014 | Kang |
| 2014/0180290 A1 | * | 6/2014 | Otto ...................... A61B 34/30 606/80 |
| 2014/0188121 A1 | * | 7/2014 | Lavallee ................. A61B 6/032 606/102 |
| 2014/0200621 A1 | * | 7/2014 | Malackowski ........ A61B 34/70 606/86 R |
| 2015/0109427 A1 | * | 4/2015 | Wood ..................... A61B 1/313 348/68 |
| 2017/0258532 A1 | | 9/2017 | Shalayev et al. |
| 2018/0049622 A1 | * | 2/2018 | Ryan .................. A61B 1/00048 |
| 2018/0168740 A1 | * | 6/2018 | Ryan ...................... A61B 34/25 |
| 2019/0076195 A1 | * | 3/2019 | Shalayev ............. A61B 18/203 |
| 2019/0090955 A1 | * | 3/2019 | Singh ...................... A61B 90/39 |
| 2019/0105514 A1 | * | 4/2019 | Amstutz ................. A61B 90/39 |
| 2019/0175283 A1 | * | 6/2019 | Bonny .................... A61B 34/20 |
| 2019/0199915 A1 | * | 6/2019 | Coiseur ................ G06K 9/3208 |
| 2019/0282123 A1 | * | 9/2019 | Crawford ............... A61B 5/061 |
| 2019/0289284 A1 | * | 9/2019 | Smith ............... A61B 1/00193 |
| 2020/0008881 A1 | * | 1/2020 | Marti ..................... A61B 90/39 |
| 2020/0129240 A1 | * | 4/2020 | Singh ....................... A61B 5/00 |

FOREIGN PATENT DOCUMENTS

| | | |
|---|---|---|
| WO | 2014045119 A2 | 3/2014 |
| WO | 2015006721 A1 | 1/2015 |
| WO | 2015/044246 A1 | 10/2015 |

OTHER PUBLICATIONS

Cohan, Steve, "ROBODOC Achieves Pinless Registration", Industrial Robot: An International Journal, 2001, pp. 381-386, vol. 28, Issue 5, © MCB UP Limited (2001); DOI: 10.1108/01439910110401277.

Godest, A.C. et al., "Simulation of a Knee Joint Replacement During a Gait Cycle Using Explicit Finite Element Analysis", Journal of Biomechanics, Feb. 2002, pp. 267-275, vol. 35, Issue 2, © 2002 Elsevier Science Ltd.; DOI: 10.1016/S0021-9290(01)00179-8.

Madera, Francisco, "An Introduction to the Collision Detection Algorithms", Abstraction & Application, 2011, pp. 7-18, vol. 5; Facultad de Matematicas, UADY; mramirez@uady.mx.

International Search Report dated Mar. 8, 2017 for International Application No. PCT/US2016/062008 filed Nov. 15, 2016.

Extended European Search Report, dated Apr. 10, 2019.

Office Action issued in corresponding Chinese Patent Appln. No. 201680065323.6, dated Jun. 3, 2020.

* cited by examiner

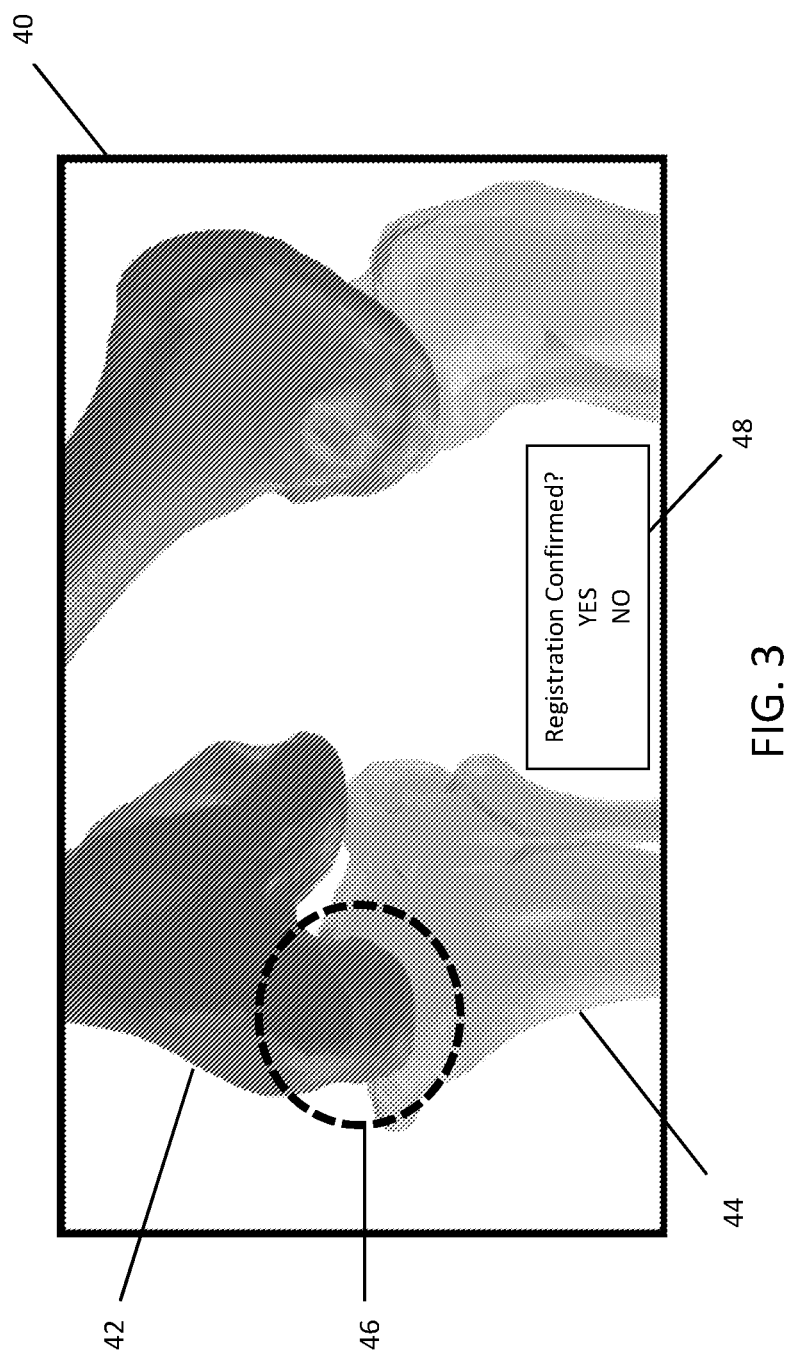

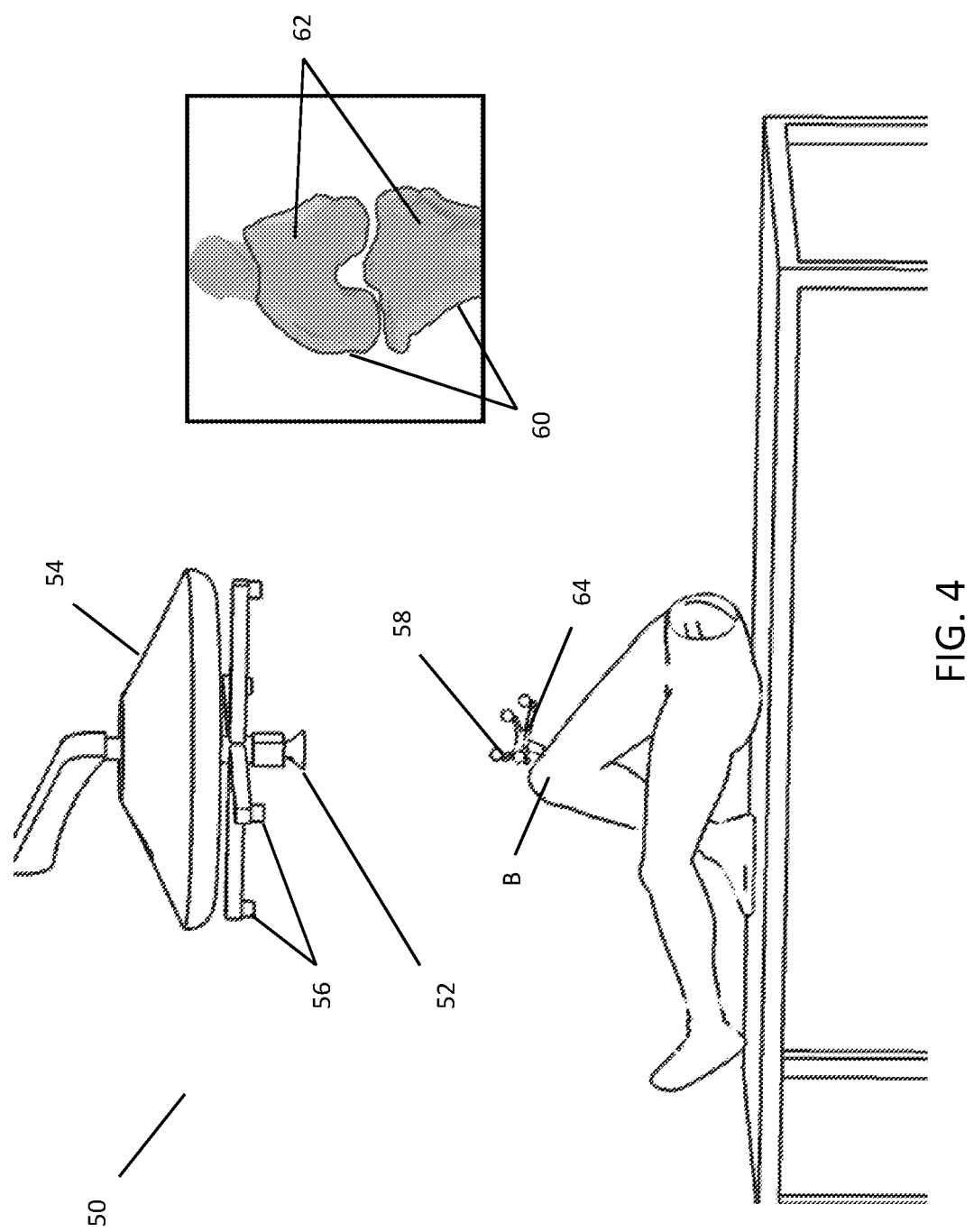

METHOD FOR CONFIRMING
REGISTRATION OF TRACKED BONES

FIELD OF THE INVENTION

The present invention generally relates to the field of computer assisted orthopaedic surgery and in particular, to a new and useful process and system for confirming registration of tracked bones in surgery.

BACKGROUND OF THE INVENTION

Total joint replacement (TJR) (also called primary total joint arthroplasty) is a surgical procedure in which the articulating surfaces of a joint are replaced with prosthetic components, or implants. TJR, especially for hips, knees, shoulders, and ankles restores functionality while greatly reducing pain associated with osteoarthritis in patients. The benefits of TJR are tempered by complications associated with replacement misfit. Less than perfect fit of a replacement joint places unbalanced forces on the implant that can lead to premature implant wear and discomfort. When such wear becomes extreme, revision surgery is required.

TJR typically involves the removal of the articulating cartilage surface of the joint including a varying amount of bone depending on the joint and the replacement implant being used. This cartilage and bone is then replaced with a synthetic, typically metal and/or plastic, implant that is used to create a new joint surface. The position, orientation and compliance of the prosthetics implanted into the joint are critical factors that have a significant effect on the clinical outcome of the patient. Therefore, computer assisted surgical devices are gaining popularity as a tool to pre-operatively plan and precisely execute the plan to ensure an accurate final position and orientation of the prosthetics within the patient's bone that can improve long term clinical outcomes and increase the survival rate of the prosthesis. In general, the computer assisted surgical systems include two components, an interactive pre-operative planning software program and a computer assisted surgical device that utilizes the pre-operative data from the software to assist the surgeon in precisely executing the procedure.

The conventional interactive pre-operative planning software generates a three dimensional (3-D) model of the patient's bony anatomy from a computed tomography (CT) or magnetic resonance imaging (MRI) image dataset of the patient. A set of 3-D computer aided design (CAD) models of the manufacturer's prosthesis are pre-loaded in the software that allows the user to place the components of a desired prosthesis to the 3-D model of the boney anatomy to designate the best fit, position and orientation of the implant to the bone. The user can then save this pre-operative planning data to an electronic medium that is loaded and read by a surgical device to assist the surgeon intra-operatively in executing the plan.

Additionally, one of the main goals of computer-assisted surgery is to define a patient specific plan and precisely execute the procedure, in a timely manner on a patient. The accuracy of the cut volume for a given implant is critical and errors can accumulate based on registration error, cutter manufacturing tolerances and implant manufacturing tolerances. Registration techniques well known in the art such as point to surface registration can align the coordinate frames of a patient's bone to the coordinate frames of a 3-D model of a patient's bone and to the coordinate frame of the surgical device.

The registration of the location of the bone intra-operatively within the workspace of a surgical robot serves to determine the precise location and orientation of the bone within the workspace of the robot. In some embodiments, this may be accomplished by probing radiopaque fiducial markers placed into or on the bone that were installed prior to pre-operative imaging. A fiducial marker is appreciated to be a material with an opacity that is different than that of surrounding subject tissue or a reference point capable of detection by an external source (e.g. optical cameras, x-rays, radio frequency). Examples of fiducial markers include a radiopaque pin, an active device such as radio frequency identification (RFID) tag or light emitting diode (LED), a passive retro-reflective sphere, or a combination thereof. In still other inventive embodiments, a registration guide is applied that fits on the bone, or a surface matching algorithm is used, or any other method to determine the orientation of the subject's operative bone. The usage of such techniques are further detailed in: PCT/IB2013/002311 entitled SYSTEM AND METHOD FOR REGISTRATION IN ORTHOPAEDIC APPLICATIONS. S. Cohan, "ROBODOC achieves pinless registration" The Industrial Robot; 2001; 28, 5; pg. 381. P. J. Besl, "A Method for Registration of 3-D Shapes" IEEE Transactions on Pattern Analysis and Machine intelligence, 1992; 14, pgs. 239-256.

Once the registration is complete, it is imperative that the registration is verified and remains accurate throughout the entire procedure. If a tracking system monitors the POSE of the registered bone via tracking arrays fixed thereto, any relative movement between the tracking array and the bone negates the accuracy of the registration. If the bone is not re-registered, the procedure cannot be executed according to the plan. Often, the tracking array is bumped unintentionally and there is no method for signaling or alerting the surgeon that the registration is no longer accurate. Or, the fixed tracking array may drift over-time accumulating errors in the registration. It is not until the surgeon notices the computer-assisted device is off-target or there is an erroneous reading on the device to suggest the registration is compromised.

Additionally, there is no intuitive visual process for verifying the accuracy of the registration. In certain registration procedures, a final verification step may be implemented which involves digitizing several additional points on the bone after the registration is complete. The additional points confirm and verify the POSE of the bone. A prompt may then indicate that the registration was successful. However, this verification process can increase the surgical time.

Finally, after the TJR is complete, the surgeon may articulate the joint to ensure the proper range of motion and kinematics are achieved. It may be desirable to restore the joint to a similar joint motion, kinematics, or articulation as the pre-cut anatomy so the soft tissues are well balanced, and there is decreased stress on the surrounding muscles and other anatomical structures. Having a process to compare the articulation of the now modified joints to the pre-articulating motion may be highly beneficial for assessing not only the outcome of the procedure, but to also provide a mechanism for recommending intraoperative modifications for the joint to achieve the pre-articulating motion.

Thus, there exists a need for a system and process to verify and monitor the accuracy of bone registration prior to and during a computer-assisted surgical procedure. There further exists a need for a process to articulate a joint prior to making any cuts, so as to compare the articulation after the trial implants are in place to see the differences, and possibly recommend corrections so as to obtain a similar articulation as the pre-cut anatomy. There further exists a need to rely on this comparison as a way to recommend adjustments to the tibial internal-external rotation in knee replacement TJR.

SUMMARY OF THE INVENTION

A process for confirming registration of bones involved in a joint replacement procedure is provided that includes a three dimensional (3-D) models of the bones being generated. The bones are tracked with a tracking device attached to each of the bones to allow 6-degrees of freedom (DOF) tracking during the joint replacement procedure. The 3-D models to the bones are registered and the bones having the tracking device are moved. A corresponding motion in the 3-D models with the moving of the bones is then observed. The registration of the 3-D models to the bone when the observations of the 3-D models move in correspondence with the actual bones is then confirmed or an alarm when an algorithm detects the 3-D bone models move unexpectedly during the movement of the bones.

A system for confirming registration of bones involved in a joint replacement procedure includes a high definition (HD) camera mounted on a surgical light. An integrated tracking system for tracking the position and orientation of each of the bones is provided. One or more marker light emitting diodes (LEDs) are fitted on each of the bones prior to registration. A display is adapted to show a three-dimensional (3-D) reconstructed picture of the bones from a perspective of said HD camera or an outline of a model of the bones superimposed on video from said HD camera.

A system for confirming registration of bones relative to a tracking system by the process includes a tracking array attached to a bone of a patient with one or more marker LEDs mounted to each of the bones. A tracking system is provided to monitor the relative position between the tracking array and the one or more marker LEDs after bone registration. The tracking system generates an alert if there is relative movement between the tracking array and one or more marker LEDs mounted on the bone.

BRIEF DESCRIPTION OF THE DRAWINGS

The present invention is further detailed with respect to the following drawings. These figures are not intended to limit the scope of the present invention but rather illustrate certain attributes thereof.

FIG. 3 illustrates a collision between 3-D models of the operative bones while a surgeon moves the actual bone;

FIG. 4 illustrates system for the verification of bone registration using a high definition (HD) camera mounted on a surgical light and including an integrated tracking system.

DESCRIPTION OF THE INVENTION

Figure 1:
FIG. 1 illustrates a 3-D model of the operative bones of a knee joint replacement procedure.

The present invention has utility as a system and process for confirming the registration of tracked bones prior to and during a computer-assisted surgical procedure. Embodiments of the inventive process and system confirm registration of a subject's bones by articulating the physical tracked bones relative to 3-D displayed models of the tracked bones. The articulation of the physically tracked bones and corresponding motion of the 3-D displayed models may be further used to adjust the bone orientation or provide intra-operative joint modification recommendations for improved artificial joint positioning, as compared to conventional techniques.

The following description of the preferred embodiments of the invention is not intended to limit the invention to these preferred embodiments, but rather to enable any person skilled in the art to make and use this invention. The invention described herein illustratively uses total knee arthroplasty as an example. Although total knee arthroplasty is one procedure that can benefit from the disclosed embodiments other surgical procedures can illustratively include surgery to the hip joint, spine, shoulder joint, elbow joint, ankle joint, jaw, a tumor site, joints of the hand or foot, and other appropriate surgical sites.

As used herein, a fiducial marker refers to a point of reference capable of detection. Examples of a fiducial marker may include: an active transmitter, such as a light emitting diode (LED) or electromagnetic emitter; a passive reflector, such as a plastic sphere with a retro-reflective film; a distinct pattern or sequence of shapes, lines or other characters; acoustic emitters or reflectors; magnetic emitters or reflectors; radiopaque markers; and the like or any combinations thereof. A tracking array is an arrangement of a plurality of fiducial markers in/on a rigid body of any geometric shape, where each tracking array has a unique geometry of fiducial markers or a unique blinking frequency if active LEDs are used to distinguish between each of the tracked objects.

Disclosed herein is the use of a tracking system. Optical tracking systems generally include at least two receivers to detect one or more fiducial markers in three-dimensional space. The receivers are in communication with at least one processor for processing the receiver output. The processing determines the position and orientation (pose) of a tracking array using various algorithms such as time-of-flight or triangulation. The receiver may detect the location of a fiducial marker through a variety of mechanisms including, but not limited to, visible light, electromagnetic radiation, and infrared, as well as any shape, pattern, line, sequence or character recognition. It should be appreciated that other tracking systems known in the art may be used to track objects using radio frequency, magnetics, accelerometers, gyroscopes, acoustic energy or signals, and mechanical linkages. Examples of tracking systems to determine the pose of an object are described in U.S. Pat. Nos. 5,282,770, 6,061,644, and 7,302,288. An example of a mechanical tracking system having mechanical linkages is described in U.S. Pat. No. 6,322,567.

Also referenced herein are computer-assisted devices which are to be considered synonymous with computer-aided surgical system, robotic surgical systems, navigation assisted surgical system, image-guided surgical systems and the like. The computer-assisted device may be, for example, a 2-6 degree of freedom hand-held surgical system, a serial chain manipulator system, a parallel robotic system, or a master-slave robotic system, as described in U.S. Pat. Nos. 5,086,401, 7,206,626, 8,876,830, and 8,961,536, U.S. Pat. App. No. 2013/0060278 and U.S. Prov. App. 62/054,009. Such commercial systems illustratively include for example the NavioPFS™ Robotic Resurfacing System (Blue Belt Technologies), the RIO® Robotic System (Mako Surgical Corp.), and the TSolution One™ Surgical System (Think Surgical). It should be appreciated that navigated or tracked instruments may also be used with the subject matter disclosed herein.

A process is provided to confirm the registration of bones involved in a joint replacement procedure. The process includes the use of pre-operative planning software to generate a 3-D model of the patient's bony anatomy from a computed tomography (CT) or magnetic resonance imaging (MRI) image dataset of the patient. A set of 3-D computer aided design (CAD) models of the manufacturer's prosthesis are pre-loaded in the software that allows the user to place the components of a desired prosthesis to the 3-D model of the boney anatomy to designate the best fit, position and orientation of the implant to the bone. This is accomplished with commercially available systems such as the RIO® Interactive Orthopedic System manufactured by Stryker Mako (Ft. Lauderdale, Fla.) and the TSolution One™ Surgical System manufactured by THINK Surgical, Inc. (Fremont, Calif.). An exemplary 3-D modeling of a joint that will be subject to replacement is illustrated in FIG. 1. FIG. 1 depicts a 3-D model of a knee joint including a coronal and sagittal view of the distal femur 12 and proximal tibia 14. The 3-D virtual models may be displayed on a monitor 10 to facilitate pre-operative planning or to monitor the motion of the tracked bones intra-operatively.

A computer simulation may be run to optimize the multiple variables of positional and rotational degrees of freedom to achieve an optimized artificial joint geometry. A finite element analysis is readily applied based on these variables to achieve a balanced force weighting on opposing sides of the joint through a preselected swing angle for the joint. It is appreciated that patient weight, height, and arm swing counterbalance are additional factors that can be built into the optimization routine to predict optimal joint arthroplasty positioning. An example of analyzing the positional and geometric rotational degrees of freedom using a computer simulated model is described in A. C. Godest et al., "Simulation of a knee joint replacement during a gait cycle using explicit finite element analysis" Journal of Biomechanics 35 (2002) 267-275.

Figure 2:
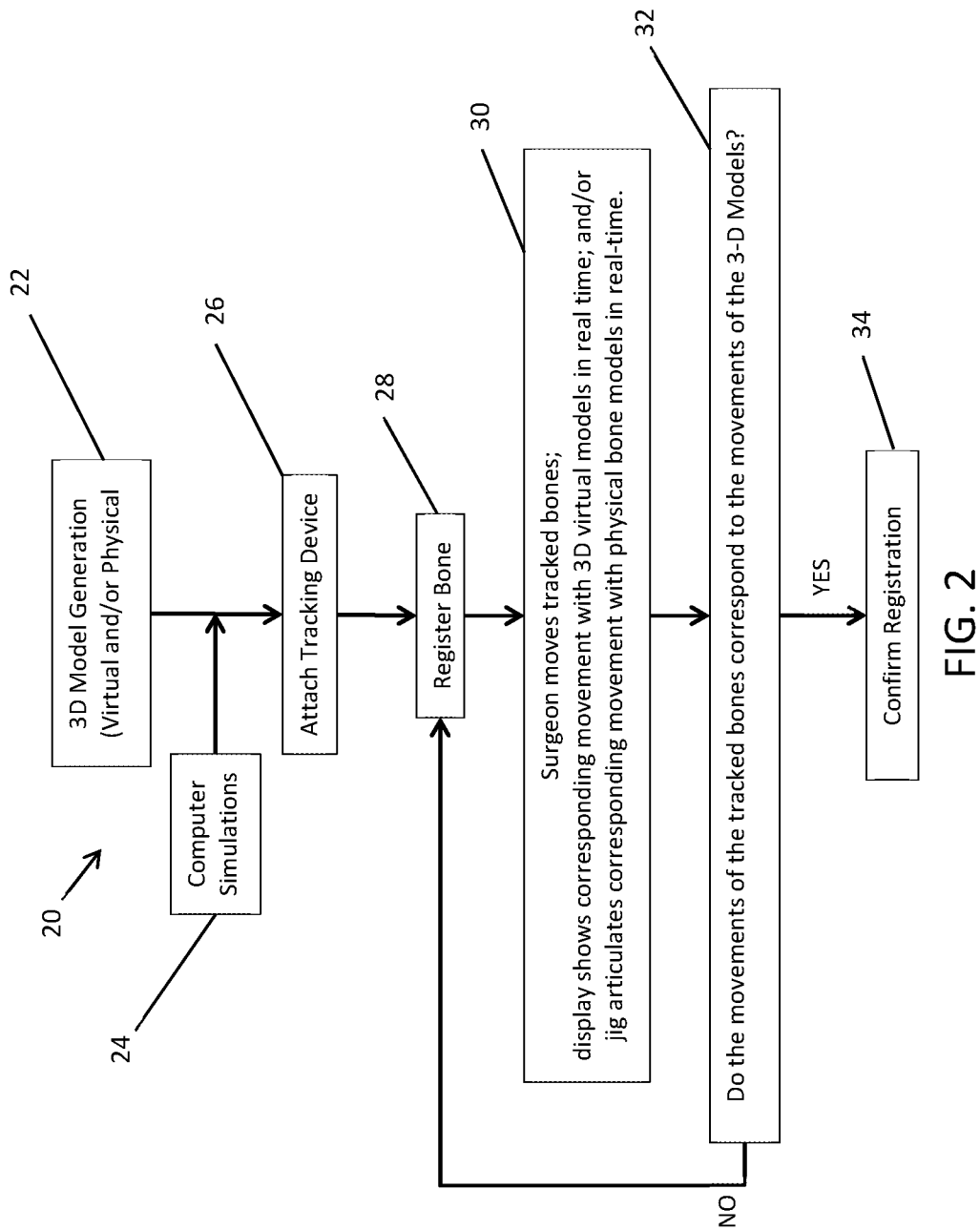
FIG. 2 illustrates a process flowchart according to the present invention.

With reference to FIG. 2, an inventive process schematic is shown generally at 20. The three dimensional (3D) models of operative bones involved in a joint replacement procedure are generated, as a physical or virtual model at step 22 and is made available to the surgeon during the procedure. The virtual models may be part of an overall surgical plan that further includes instructions for a computer-assisted surgical device, the final implant position, or the results of any such computer simulations generated for the optimal position of the bones or implants at step 24.

A tracking device such as a tracking array or a mechanical tracking probe is attached to each operative bone to allow 6-degrees of freedom (DOF) tracking during the procedure at 26. The bones may be tracked by a tracking system as previously described. The 3D models of each operative bone are then registered to the patient's actual operative bone at step 28. Systems and methods of optical or mechanical tracking and registration are described in U.S. Pat. No. 6,033,415, which is incorporated herein by reference in its entirety. Systems and processes for pre-operative planning and precise bone removal are also known to the art and include those detailed in WO 2015006721 A1.

At step 30, the surgeon moves a tracked bone having a tracking device associated therewith, and a display shows a virtual representation of the motion in real-time. As a result, a surgeon can observe the position of the bones involved in the joint arthroplasty in a way that is impossible from viewing the actual bones. This attribute of the present invention is a novel attribute that becomes increasingly helpful as the bones tagged with a tracking device approach the optimal positioning. In some inventive embodiments, the display or jig include feedback indicators such as markers, a blinking screen, arrows, or highlighted areas on the virtual bone models, that may be used to indicate or guide the surgeon to an optimal position and orientation of a given bone based on the pre-surgical plan and any simulations associated therewith. The surgeon may then assess the kinematics of the operative bones in the position and orientation defined by the pre-surgical plan prior to making any bone cuts.

In a particular embodiment, the surgeon or system determines if the movements of the tracked bones correspond to the movements of the 3-D models at step 32. If the tracked bones are moving in correspondence with the 3-D models then the surgeon can confirm that the registration is accurate at step 34. If the tracked bones do not move in correspondence with the 3-D models, or the motion is unexpected, then the accuracy of the registration is likely not accurate. In that case, the surgeon re-registers the bone. This is described in more detail below.

In an illustrative example of a specific applications of the invention, with respect to FIG. 3, the surgeon may verify or confirm the accuracy of the registration by making sure that the tracked femur and tibia do not collide by viewing the 3-D models on a display 40 (e.g. monitor, television); or that the femoral head stays approximately in the center of the acetabulum during articulation of the femur relative to the pelvis, each tracked, by viewing the 3-D models on the display 40 during articulation. This provides an intuitive visual process for confirming the accuracy of the bone registration. If, for example, the 3D virtual model of the femur 42 appears to impinge or collide with the 3D virtual model of the tibia 44 throughout articulation as seen in the bounding circle 46, or the femoral head rotates outside the center of the acetabulum, then the registration is likely not accurate and the surgeon can re-register the bone before proceeding with the procedure. If the registration appears accurate, the surgeon may confirm or verify the registration by way of an input mechanism (e.g. mouse, keyboard, joystick, pendant, touchscreen display, microphone) in communication with the tracking system or computer-assisted device. A prompt 48 may be displayed on the display 40 for the surgeon to select whether the registration is confirmed or not. The surgeon may also confirm the registration to the system or device by providing a particular signal to the tracking system. For example, the surgeon can place a tracked digitizer probe in a specific location relative to the 3-D bone model, or manipulate the bones in a particular pattern or shape. Therefore, the surgeon to quickly confirm the registration without having to use an input mechanism.

It should be appreciated that the surgeon can monitor and confirm the registration throughout an entire procedure by moving the tracked bones and visualizing the corresponding motion of the 3-D virtual models on the display. In certain applications, such as TKA, articulating the joints throughout flexion/extension are normal steps of the procedure. Therefore, confirming the registration throughout these normal procedural steps is quick, efficient, and does not require any additional steps outside of a normal TKA. Additionally, by viewing such models devoid of skin, connective tissue, fat, and blood provides insights not available to a surgeon through actual inspection of the joint before or during surgery.

In an inventive embodiment, collision detection may be implemented with a computer program or through other types of algorithms that provide a warning to a surgeon or other medical personnel if the 3D virtual models collide during the articulation of the tracked bones. One example of a collision detection algorithm that can be modified by one of skill in the art to warn a surgeon of inaccurate registration is described in Madera-Ramírez, Francisco. "An Introduction to the Collision Detection Algorithms." *Abstraction and Application Magazine* 5 (2014). Other algorithms can also be implemented to provide a warning or alert the surgeon that the corresponding motion of the 3-D virtual models is outside of specified thresholds. For example, the algorithm may monitor the relative rotation of the femur with respect to the center of the acetabulum. If the femoral head does not rotate within ±2 mm of the natural center of the acetabulum, then an alert may be generated. In another example, an alert be generated if the bone models move apart beyond a threshold limit. In TKA, if the closest point between the tibia and either the medial or lateral condyle region of the distal femur becomes significantly greater than the expected total cartilage thickness or other specified distance threshold, the registration is likely off or the tracking arrays may have moved relative to the bone, and an alert is generated.

In certain inventive embodiments, registration of tracked bones may also be confirmed by observing the full extension position of a subject's limb and compare the limb extension to the virtual full extension position to make sure that the achieved extension is correct. Furthermore, as a comparison control, a measurement of the articulation of the joint prior to making any surgical or altering cuts may be saved for later comparison with a post treatment or operative articulation for a measurement of alignment after the trial implants are in place to see the differences, and possibly recommend corrections. As a result, a surgeon can obtain joint positions that retain pre-cut bone positions or controlled modification of dysfunctional pre-cut geometries. In a specific inventive embodiment, a pre- and post-operative comparison may be used as a way to recommend adjustments for the subject's tibia internal-external rotation.

Furthermore, surgical errors during bone resection may lead to abnormal joint motion after trial implantation, and specific embodiments of the invention are used to visualize the abnormal joint motion, where the operative bones, with trial implants, are tracked during motion, and 3-D models of the pre-operative bones are displayed rather than the post-operative bones. Any abnormal motion, such as collisions between the bones, would indicate changes in joint kinematics and may be used to direct the surgeon's choice of intraoperative correction For example, in TKA, if a collision detection algorithm detects ±2 mm of collision in varus-valgus rotation between the medial femoral condyle and the medial aspect of the tibia, the computer-assisted device or tracking system may recommend to the surgeon via a prompt on a display, that 2 mm of the medial aspect of the tibia should be resected to obtain the pre-cut articulating motion of the knee. These recommendations can be extended to other alignment characteristics such as the tibial slope, internal-external rotation of the femoral or tibial component, varus-valgus rotation, mechanical axis alignment, kinematic alignment, ligament balancing, soft tissue balancing, flexion/extension gap, and any combinations thereof to achieve the pre-cut anatomical articulation.

Figure 7:
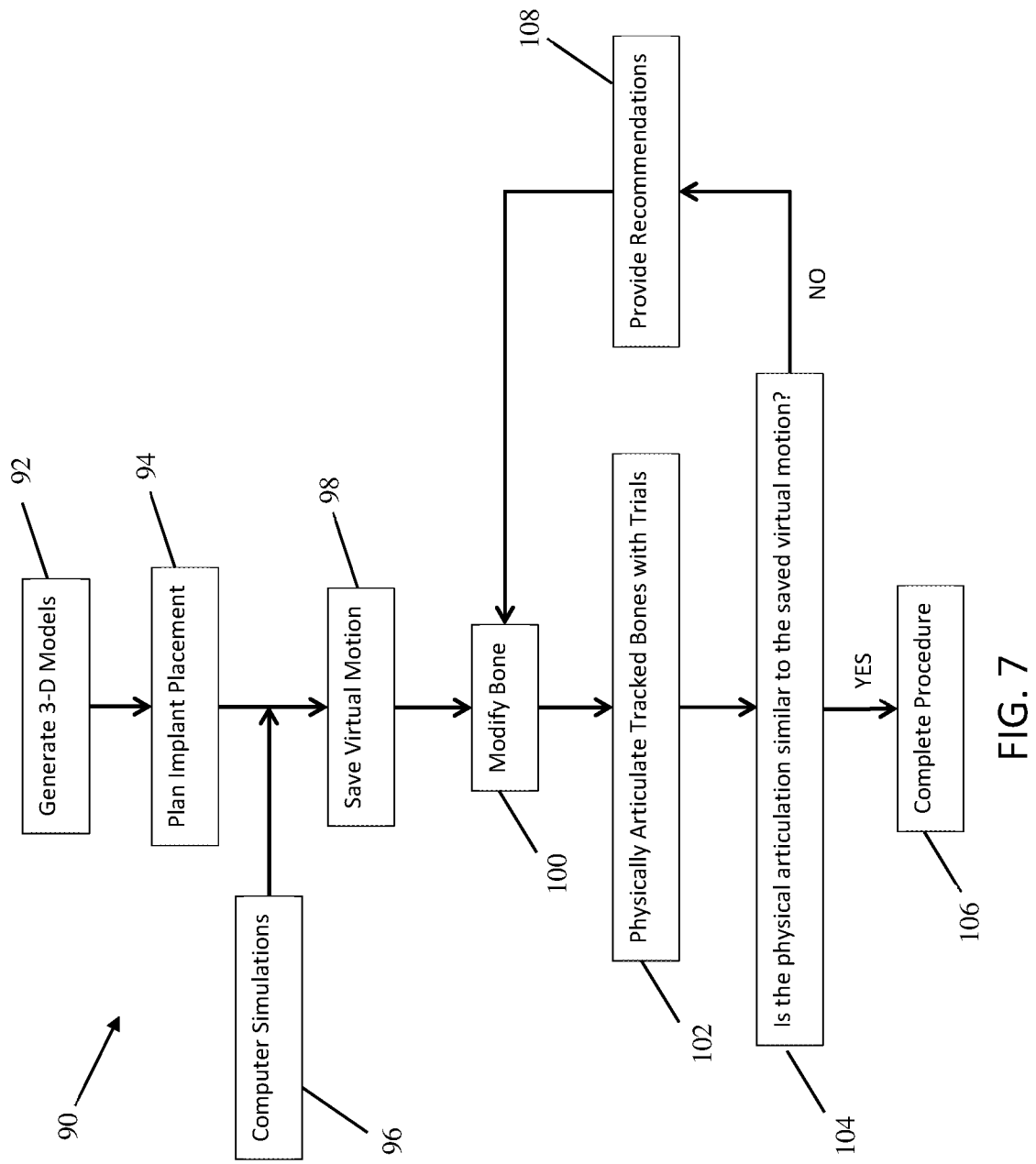
FIG. 7 illustrates a process flowchart for comparing a virtual motion to a physically tracked bone motion according to embodiments of the invention.

FIG. 7 generally outlines another process 90 using the physical articulation of the tracked bones to provide bone modification recommendations and/or further aid a surgeon in obtaining a pre-operatively planned result. The generation of the 3-D bone models (step 92), and the planning of the placement of the virtual implants relative to the bone models (step 94) with or without the aid of the computer simulations (step 96), are all accomplished as described above. Next, the virtual motion of the 3-D bone models with the virtual implants is simulated. The surgeon may further adjust the planned position of the virtual implants to achieve a desired virtual motion that the surgeon prefers the actual bone motion to mimic post-operatively. The desired virtual motion is then saved at step 98 for use intra-operatively. At step 100, the surgeon executes the procedure and modifies the bone according to the plan as described above. After modifying the bone, trial components are placed in the joint and the surgeon physically articulates the tracked bones at step 102. The saved virtual motion is then compared with the actual articulation of the tracked bones at step 104. In a specific embodiment, the saved virtual motion of the 3-D bone models with the virtual implants are overlaid on the 3-D bone models registered to the actual bones. To ensure the saved virtual motion corresponds with the physical motion, one of the virtual bones or a portion of one of the virtual bones is mapped to one of or a portion of the 3-D bone model registered to the actual bone. For example, the femoral head and neck of the pre-operative virtual model associated with saved virtual motion is mapped to the femoral head and neck of the virtual model registered to the bone. Therefore, the surgeon can observe how the actual motion of the non-mapped bone corresponds to the saved virtual motion of the non-mapped bone. For TKA, the mapped bone may be the femur, where the surgeon can observe how the actual tibia moves in relation to the actual femur and compare this to how the virtual tibia moved relative to the virtual femur during planning. The surgeon may have the ability to speed-up and slow-down the virtual motion, or stop the virtual motion at particular articulation points, to aid in the comparison. If the motions are similar, the surgeon can complete the procedure (step 106) by inserting the final implants and closing the surgical site. If the motions are dissimilar, the computer-assisted system may provide recommendations (step 108) to re-modify the bone such that the actual bone motion corresponds with the saved virtual motion.

In FIG. 4, a particular embodiment of a system is shown generally at 50 for facilitating embodiments of the aforementioned processes including the confirmation, verification and monitoring of bone registration. The system 50 may include a high definition (HD) camera 52 mounted on a surgical light 54 that has an integrated tracking system with optical receivers 56. The HD camera 52 may be calibrated to a tracking system using one or more marker light emitting diodes (LEDs) 58 fitted on the bone B prior to registration, and then during a post-registration assessment, a 3D reconstructed picture of the bone model from the HD camera's perspective, or an outline of the bone model 60 from that perspective, could be superimposed on the video 62 from the camera 52, and this should visually correspond to the image of the bone B in the video 62. If, for example, the tracking array 64 on the bone B should move, or be bent during the procedure, the superimposed bone model 60 would shift away from being aligned with the bone B in the video 62. This would give the surgeon an easily checked indication in real-time of whether the registration is still fundamentally accurate.

Figure 5B:
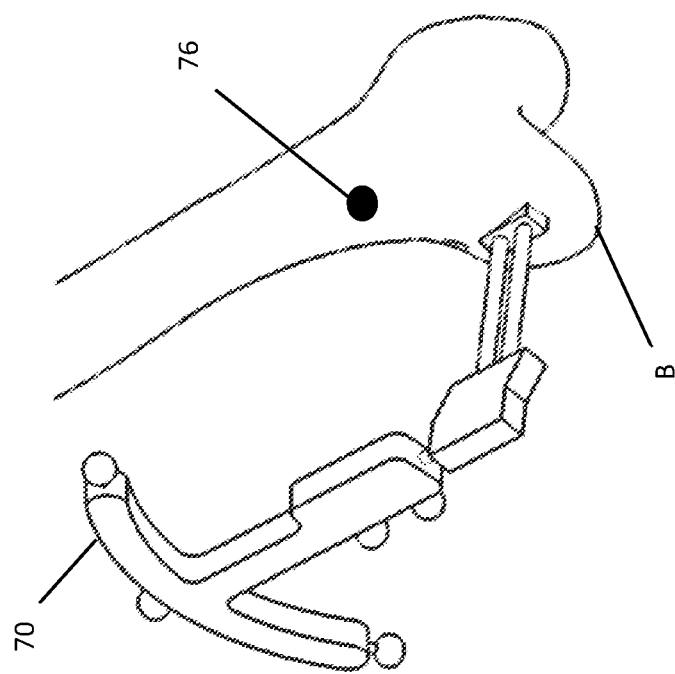
FIGS. 5A and 5B, illustrates a tracking array with an LED that highlight a relative position on the operative bone to monitor registration accuracy.
Figure 5A:
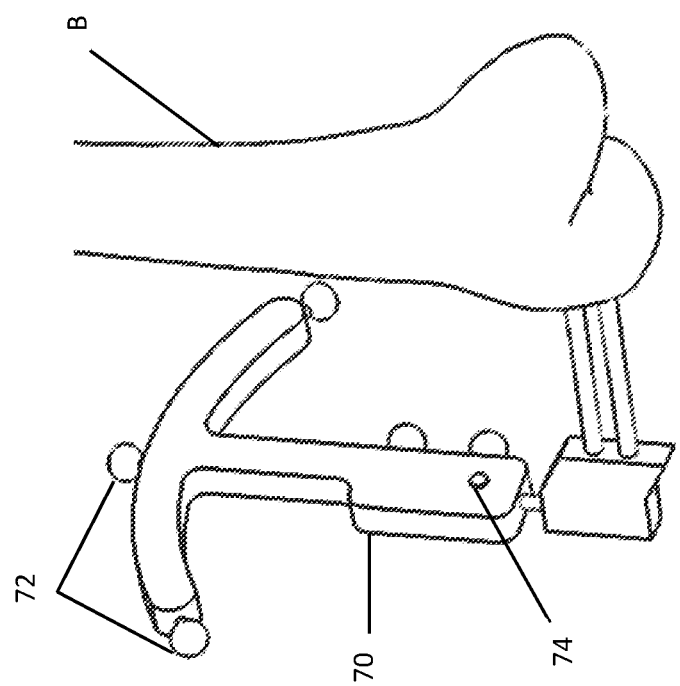

In a specific inventive embodiment, with respect to FIGS. 5A and 5B, an LED 74 on the tracking array 70 is used to illuminate a particular landmark or manually made mark 76 on the bone B. The tracking array 70 shown here includes passive fiducial markers 72 and an LED 74 capable of highlighting an arbitrary spot on the bone B. For example, once the tracking array 70 is attached to the bone B, this LED 74 illuminates a small spot in an arbitrary location on the bone B, the surgeon would then mark that spot 76 with a marking device, illustratively including a purple pen, and then proceed to do the registration. If the tracking array 70 moves relative to the bone B during registration or the procedure, the highlighted spot will almost certainly move away from the marked purple spot 76, indicating a registration error. In a specific inventive embodiment, a distance measurement device, illustratively including a laser or possibly an LED mechanism 74 may be attached to the tracking array 70. The distance measurement device may be pointed at the bone and would detect a change in distance if the tracking array moved relative to the bone.

Figure 6:
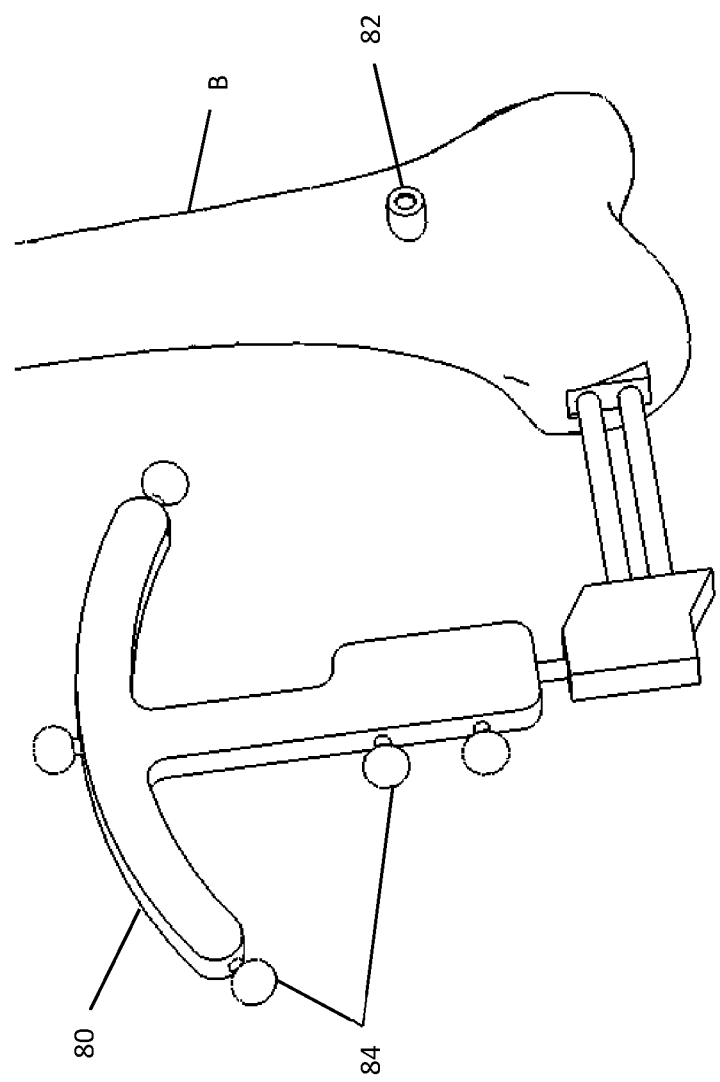
FIG. 6 illustrates a single fiducial marker mounted on the bone relative to a tracking array attached to the bone to monitor registration accuracy.

In an inventive embodiment, with respect to FIG. 6, a single fiducial marker 82 is mounted on the bone B, in relation to a tracking array 80 attached to the bone to provide a redundant reference for monitoring any relative motion between the fiducial marker 82 and the tracking array 80. After registration, if the tracking array 80 were to move or bend, the tracking system would see the geometry change between the tracking array markers 84 and the single fiducial maker 82. An alarm or prompt may be triggered to alert the surgeon that the tracking array 80 has moved relative to the bone indicating the registration is no longer accurate. In an embodiment, the fiducial marker 82 may be a single LED powered with a small embedded battery, which would most likely be a disposable battery.

In specific inventive embodiments, two full markers are attached to a bone at a given location, with a main marker and a smaller, less accurate marker, to check that the relative transform between the markers remains stable. Furthermore, a digitizer may be used as needed to recheck a particular landmark or manufactured mark, such as a purple pen mark, if any question on the registration arises.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The foregoing description is illustrative of particular embodiments of the invention, but is not meant to be a limitation upon the practice thereof. The following claims, including all equivalents thereof, are intended to define the scope of the invention.

The invention claimed is:

1. A process for confirming registration of bones involved in a joint replacement procedure, said process comprising:
generating a three dimensional (3-D) models of the bones involved in the joint replacement procedure;
tracking the bones with a tracking device attached to each of the bones involved in the joint replacement procedure to allow 6-degrees of freedom (DOF) tracking during the joint replacement procedure;
registering the 3-D models to the bones involved in the joint replacement procedure;
moving the bones having the tracking device;
observing a corresponding motion in the the 3-D models with said moving of the bones involved in the joint replacement procedure; and
confirming the registration of the 3-D models to the bones involved in the joint replacement procedure when the observations of the 3-D models move in correspondence with the bones involved in the joint replacement procedure or providing an alarm when an algorithm detects the 3-D bone models move unexpectedly during the movement of the bones involved in the joint replacement procedure.

2. The process of claim 1 wherein the 3-D models are virtual and said observing is on a video display.

3. The process of claim 1 wherein the registration is confirmed to a computer-assisted surgical system using an input mechanism in communication with the computer-assisted surgical system.

4. The process of claim 1 further comprising re-registering the 3-D models to the bones involved in the joint replacement procedure if the observations of the 3-D bone models collide.

5. The process of claim 1 further comprising re-registering the 3-D models to the bones involved in the joint replacement procedure if the observations of the 3-D models rotate outside of a known anatomical region.

6. The process of claim 5 wherein the bones involved in the joint replacement procedure are a femur and an acetabulum and the 3-D models are re-registered when the observations of the femur 3-D model rotates outside the center of the acetabulum 3-D model.

7. The process of claim 1 further comprising re-registering the 3-D models if the observations of a first 3-D bone model is separated from a second 3-D bone model beyond a specified threshold distance.

8. The process of claim 7 wherein the specified threshold distance is an expected cartilage thickness on an end of one or more bones involved in the joint replacement procedure.

9. The process of claim 1 further comprising simulating operation of the bones involved in the joint replacement procedure as a joint to yield an optimal configuration and displaying the optimal configuration on the corresponding motion in the 3-D models.

10. The process of claim 1 wherein the said alarm is present providing an alarm when an algorithm detects the 3-D bone models move unexpectedly during the movement of the bones involved in the joint replacement procedure.

11. The process of claim 10 wherein the unexpected movements of the 3-D bone models is a movement beyond a specified threshold distance between the 3-D bone models.

12. The process of claim 11 wherein the specified threshold distance is a distance greater than an expected cartilage thickness.

13. The process of claim 10 wherein the bones involved in the joint replacement procedure are a femoral head and an acetabulum and the unexpected movements of the 3-D bone models is a rotation of the femoral head 3-D model outside of the center of the acetabulum 3-D model.

* * * * *